United States Patent

Schmidt et al.

Patent Number: 5,266,581
Date of Patent: Nov. 30, 1993

[54] SOLID COMPOSITION CONTAINING DIHYDROPYRIDINE, PVP AND PVPP

[75] Inventors: Wolfgang Schmidt, Cologne; Helmut Luchtenberg, Niederkassel; Eduard Porges, Cologne, all of Fed. Rep. of Germany

[73] Assignee: Bayer Aktiengesellschaft, Leverkusen, Fed. Rep. of Germany

[21] Appl. No.: 12,119

[22] Filed: Feb. 1, 1993

Related U.S. Application Data

[63] Continuation-in-part of Ser. No. 467,316, Jan. 18, 1990, abandoned, which is a continuation of Ser. No. 750,566, Jun. 27, 1985, abandoned.

[30] Foreign Application Priority Data

Jul. 4, 1984 [DE] Fed. Rep. of Germany ....... 3424553

[51] Int. Cl.⁵ .......................................... A61K 31/44
[52] U.S. Cl. ................................ 514/356; 514/772.3; 514/772.7
[58] Field of Search ...................... 514/356; 424/772.3, 424/772.7

[56] References Cited

U.S. PATENT DOCUMENTS

| Re. 33,963 | 6/1992 | Hegasy | 424/78.24 |
| 3,784,684 | 1/1974 | Bossert et al. | 424/37 |
| 4,412,986 | 11/1983 | Kawata et al. | 424/80 |
| 4,882,144 | 11/1989 | Hegasy | 424/86 |
| 4,892,730 | 1/1990 | Hegasy | 424/80 |
| 4,981,683 | 1/1991 | Hegasy | 424/80 |

FOREIGN PATENT DOCUMENTS 0001247 4/1979 European Pat. Off. .
1173862 12/1969 United Kingdom .

Primary Examiner—Allen J. Robinson
Attorney, Agent, or Firm—Sprung Horn Kramer & Woods

[57] ABSTRACT

A solid, rapidly absorbable composition by weight consisting of 1 part by weight of nimodipine, 0.01 to 1.5 parts of polyvinylpyrrolidone with an average molecular weight of 15,000 to 50,000 and 1 to 12 parts by weight of crosslinked insoluble polyvinylpyrrolidone.

6 Claims, No Drawings

SOLID COMPOSITION CONTAINING DIHYDROPYRIDINE, PVP AND PVPP

This application is a continuation-in-part of application Ser. No. 467,316, filed Jan. 18, 1990, now abandoned, which is a continuation of application Ser. No. 750,560, filed Jun. 27, 1985, now abandoned.

The present invention relates to particular rapidly absorbable solid medicament formulations containing dihydropyridines, polyvinylpyrrolidone and cross-linked polyvinylpyrrolidone, and a process for their preparation.

Dihydropyridines and their calcium-antagonistic action are known (compare British Patent 1,173,862 and British Patent 1,358,951). Many representatives of this class of substance are very sensitive to light and have an extremely low solubility in aqueous media. For example, the water-solubility of nifedipine is only 10 mg per liter, and the water-solubility of nimodipine is only 2 mg per liter. Because of these particular properties, a number of difficulties occur in formulating galenical preparations, as can be seen from numerous patent applications for particular formulations of these active compounds.

U.S. Pat. No. 3,784,684, for example, relates to particular bitable gelatine capsules which contain nifedipine in dissolved form in order to utilize the coronary action of nifedipine advantageously. British Patent 1,456,618 describes and claims solid medicament formulations which are said to ensure a good bioavailability of the dihydropyridines.

DT-OS (German Published Specification) 2,822,882 likewise describes solid medicament formulations, in which the sparing solubility of dihydropyridines is said to be compensated by using certain solubilizing agents and surface-active substances.

The absorbability of nifedipine is also said, in EP-OS (European Published Specification) 1,247, to be improved by using polyethylene glycol (PEG) and certain porous carrier substances. That application also states that the poor solubility of nifedipine can be compensated by forming co-precipitates from nifedipine and polyvinylpyrrolidone (PVP), in which the nifedipine is present in amorphous form as a solid solution.

These co-precipitates are prepared by dissolving nifedipine and PVP in organic solvents, with subsequent evaporation of the solvent in order to obtain a vitreous composition (compare DT-OS (German Published Specification) 2,822,882). Such evaporation of the organic solvent can be carried out industrially only with great expenditure, since the PVP composition strongly binds the organic solvent and becomes very viscous shortly before drying. A voluminous foamy composition forms and, shortly before the end of drying, is very viscous, can no longer be stirred and can be further processed only with difficulty. Complete removal of the solvent from the co-precipitate is virtually impossible. Another disadvantage in using a nifedipine-PVP co-precipitate in the production of tablets is the fact that although this co-precipitate can be mixed with other auxiliaries, it cannot be granulated with aqueous solutions. However, such a simple mixture between the PVP co-precipitate and other auxiliaries tends to demix during further mechanical processing, for example to form tablets or during filling of capsules. In the end effect, this can lead to medicament formulations with a very different content of active compound in individual tablets or capsules (deficient "content uniformity"), which is extremely undesirable with a highly active substance such as nifedipine. Moreover, the additional auxiliaries which are available for selection are very limited, especially for the production of tablets, because PVP acts at the same-time as a binder, and the disintegration of the tablets or capsules is prevented by the presence of relatively large amounts of PVP (30 to 100 mg per tablet or capsule).

According to DE-OS (German Published Specification) 3,142,853, the disadvantages mentioned above are eliminated by using a larger amount of auxiliaries for absorption of the solution containing dihydropyridine and polyvinylpyrrolidone/acetone. Such formulations are acceptable if the active compounds are to be used only in low dosages.

However, if higher dosages, for example 30 or 100 mg of active compound, are to be used, this method has the disadvantage that the ratio of active compound to auxiliary must remain constant and very large formulation forms are thus obtained, which the patients find difficult to take (for example tablets weighing 2 g).

The present invention relates to new solid dihydropyridine formulations with a rapid absorbability and a uniform content of active compound, the relative standard deviation of which is at most 1.5%, containing 1 part by weight of dihydropyridine as acitve substance, 0.01 to 1.5 parts by weight of polyvinylpyrrolidone (PVP) with an average molecular weight of 15,000 to 50,000 and as stabilizer 1 to 12 parts by weight of cross-linked insoluble polyvinylpyrrolidone (PVPP) as adsorbant and as disintegrant, and, if appropriate, other customary auxiliaries.

As to such ingredients other than dihydropyridine, polyvinylpyrrolidene and insoluble polyvinylpyrrolidone, advantageously none is present in significantly greater amount than the dihydropyridine. Such other ingredients, particularly cellulose and starch and their derivatives, may be present in less than about half the weight of the dihydropyridine, all contributing to the relatively small size of pills or tablets made therefrom.

Accordingly, as employed herein, "consisting essentially of" identifies compositions which, beyond the stated amounts of polyvinylpyrrolidones, contain no more of individual other ingredients, and preferably no more in total of other ingredients, than the mass of the dihydropyridine.

Medicament formulations which contain the dihydropyridine-active compound in a dosage of 1 to 100 mg, in particular 5 to 70 mg, may be mentioned as preferred.

Preferred dihydropyridines which may be are compounds of the general formula I

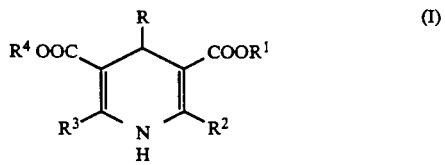

in which
R represents phenyl, which is substituted by one or two identical or different substituents from the group comprising nitro, chlorine, $CF_3$, $OCHF_2$ and =N—O—N=, $R^1$ and $R^4$ are identical or different and each represent alkyl (1–10 C atoms), which is optionally substituted by alkoxy (1–4 C atoms), fluorine, chlorine or an N-methyl-N-benzyl group, and $R^2$ and $R^3$ are identical or different and each represent alkyl (1–4 C atoms), which is optionally substituted by hydroxyl, or represent cyano.

Those formulation forms which contain a dihydropyridine from the group comprising nifedipine, nimodipine, nitrendipine, nisoldipine, nicardipine and felodipine are of particular importance.

Those formulation forms which contain 0.05 to 1.5 parts by weight, in particular 0.1 to 1 part by weight, of PVP and 2 to 8 parts by weight, in particular 2 to 6 parts by weight, of PVPP per part by weight of dihydropyridine are to be singled out.

Preferred auxiliaries which may be mentioned are: wetting agents, such as, for example, sodium laurylsulphate and Tween ®, these wetting agents being employed in a maximum amount of 1 part by weight. There may also be mentioned: lubricants, such as, for example, magnesium stearate. The presence of fillers, such as sugars, for example lactose and mannitol, glycocol, calcium carbonate, corn starch and Avicel, may also be advantageous. If appropriate, the tablets can also additionally contain disintegrating agents or can be subsequently provided with a customary lacquering in order to achieve, in the formulation according to the invention, immediate solubility, retardation or resistance to gastric juice. The formulations according to the invention, in particular the granules, can furthermore be combined with other galenical forms containing the same or different active compounds.

The solid formulation according to the invention is prepared by a procedure in which 1 part by weight of dihydropyridine and 0.01 to 1.5 parts by weight of PVP are dissolved in a corresponding amount of organic solvents in which the two solid constituents can be dissolved, a wetting agent is suspended or dissolved therein, if appropriate, and this solution is granulated with 1 to 10 parts by weight of PVPP and the resulting granules are further processed to solid medicament formulations, if appropriate after addition of further auxiliaries.

Preferred solid medicament formulations which may be mentioned are: tablets, pills, dragees, granules, powders, capsules, sachets and pellets.

Preferred organic solvents which may be mentioned are: ethanol, methanol, acetone, methylene chloride and chloroform and mixtures of these solvents. They are preferably employed in amounts of 6 to 50, in particular 8 to 20, parts by weight, based on the dihydropyridine.

It could not be predicted that the medicament formulations thus obtained retain a very good bioavailability and at the same time a good content uniformity. The granules consisting of the PVPP wetted with dihydropyridine-PVP solution which are obtained by the process according to the invention can be dried, sieved, further processed, mixed with other auxiliaries and compressed to form tablets without problems. The bioavailability of the formulations according to the invention is at least equivalent to that of the formulations known hitherto in respect of speed and level. It moreover has the advantage that the process can be carried out with very little energy and in a short time. The easy drying and the shorter drying time associated therewith (at most 20% of the conventional drying time) should be particularly emphasized. The solid formulations obtained are very small and, in spite of their high content of active compound, can also be taken by the patient without trouble.

Due to the low PVP content, drying of the moist granules is effected in a considerably shorter time (maximum of 20% of the conventional drying time). For the same reason, no lumps occur during drying.

In contrast to known formulations, which are prepared by granulation with organic solvents, the residual solvent contents are so greatly reduced by the present invention that they are below 0.05% and thus virtually can no longer be detected by conventional analytical methods. This reduction in residual solvent content is advantageous from the toxicological point of view, especially for long-term treatments.

Tablets produced in this manner have disintegration times of less than 5 minutes. Auxiliaries are saved by the process according to the invention, and not only is oral administration thereby facilitated but at the same time the production costs are also reduced.

EXAMPLE 1

30 g of nimodipines and 17 g of PVP 25 are dissolved in 500 g of acetone, and 0.5 g of sodium laurylsulphate is suspended in the solution. 107 g of crosslinked PVPP is granulated with this solution in a granulating apparatus. The granules are dried and sieved. After admixing 1.5 g of magnesium stearate, the granules are compressed to form tablets weighing 156 mg and each containing 30 mg of nimodipine. The tablets are distinguished by a low weight, good disintegration times and advantageous release.

EXAMPLE 2

The granules obtained in Example 1 are compressed to form tablets weighing 520 mg and each containing 100 mg of nimodipine.

EXAMPLE 3

30 g of nimodipine and 4 g of PVP 25 are dissolved in 800 g of acetone, and 0.5 g of sodium lauryl sulphate is suspended in the solution. 180 g of crosslinked PVPP are granulated with this solution in a granulating apparatus. The granules are dried, sieved and, after admixing 2.0 g of magnesium sulphate/ compressed to form tablets weighing 216 mg and each containing 30 mg of nimodipine.

EXAMPLE 4

30 g of nimodipine, 45 g of PVP 25 are dissolved in 500 g of acetone, and 0.5 g of sodium laurylsulphate is suspended in the solution. 120 g of crosslinked PVPP are granulated with this solution in a granulating apparatus. The granules are dried, sieved and, after admixing 1.5 g of magnesium stearate, pressed to tablets weighing 197 mg and each containing 30 mg of nimodipine.

EXAMPLE 5

The granules from Example 1 are milled or briquetted and capsules or sachets are filled with the granules obtained after sieving.

EXAMPLE 6

The solvent acetone described in Example 1 is replaced by the same amount of methylene chloride or chloroform or a mixture thereof.

EXAMPLE 7

20 g of nitrendipine, 15 g of PVP 25 and 1.5 g of Tween 80 are dissolved in acetone. 110 g of crosslinked PVPP are granulated with this solution in a granulating apparatus. The granules are dried and sieved. A mixture of 20 g of Avicel, 10 g of corn starch and 1.5 g of magnesium stearate is added as an after-mixture. The mixture is pressed to tablets weighing 178 mg and each containing 20 mg of nitrendipine.

EXAMPLE 8

This example is as Example 7, but instead of the after-mixture, granules obtained from 30 g of lactose, 20 g of Avicel and 5 g of corn starch by aqueous granulation are added. The two granules are mixed, lubricated with 1.5 g of magnesium stearate and pressed to tablets weighing 203 mg.

EXAMPLE 9

10 g of nifedipine and 5 g of PVP are dissolved in 100 g of acetone. 80 g of crosslinked PVPP are granulated with this solution in a granulating apparatus. The granules are dried and sieved. After admixing 1.0 g of magnesium stearate, the granules are compressed to form tablets weighing 96 mg. The 10 mg nifedipine tablets are distinguished by good disintegration, low weight and advantageous release.

EXAMPLE 10

10 g of nifedipine and 5 g of PVP are dissolved in a mixture of 100 g of acetone and 4 g of ethanol. A mixture of 80 g of crosslinked PVPP, 19 g of Avicel and 15 g of corn starch is granulated with the solution in a granulating apparatus. The granules are dried, sieved and mixed with an after-mixture consisting of 10 g of Avicel, 10 g of crosslinked PVPP and 1 g of magnesium stearate and compressed to form tablets weighing 150 mg and each containing 10 mg of nifedipine.

EXAMPLE 11

This example is as Example 9, with the addition of 1.0 g of Tween 80®, giving 10 mg nifedipine tablets weighing 151 mg.

The tablets and capsules are taken in the same amount as prior tablets having the same amount of active material.

It will be understood that the specification and examples are illustrative but not limitative of the present invention and that other emobidments within the spirit and scope of the invention will suggest themselves to those skilled in the art.

We claim:

1. A solid, rapidly absorbable composition by weight consisting of 1 part by weight of nimodipine, 0.01 to 1.5 parts of polyvinylpyrrolidone with an average molecular weight of 15,000 to 50,000 and 1 to 12 parts by weight of crosslinked insoluble polyvinylpyrrolidone.

2. A solid, rapidly absorbable composition by weight consisting of 1 part of a dihydropyridine, 0.01 to 1.5 parts polyvinylpyrrolidone with an average molecular weight of 15,000 to 50,000, 1 to 12 parts by weight of crosslinked insoluble polyvinylpyrrolidone, the dihydropyridine being selected from the group consisting of nifedipine, nimodipine, nitrendipine, nisoldipine and felodipine optionally sodium lauryl sulfate and optionally magnesium stearate.

3. A composition according to claim 2, containing 0.05 to 1.5 parts by weight of polyvinylpyrrolidone and 2 to 8 parts by weight of crosslinked insoluble polyvinylpyrrolidone.

4. A composition according to claim 2, containing 0.1 to 1 part by weight of polyvinylpyrrolidone and 2 to 6 parts by weight of crosslinked insoluble polyvinylpyrrolidone.

5. A composition according to claim 2, free of solvent.

6. A unit dose of a composition according to claim 2, in the form of granules, powders, a tablet or dragee.

* * * * *